United States Patent [19]
Ansmann et al.

[11] Patent Number: 5,840,943
[45] Date of Patent: Nov. 24, 1998

[54] POLYOLPOLYHYDROXYSTEARATES

[75] Inventors: Achim Ansmann, Erkrath; Rolf Kawa, Monheim; Rainer Von Kries, Illertissen; Gabriele Strauss, Duesseldorf, all of Germany

[73] Assignee: Henkel Kommanditgesellschaft auf Aktien, Duesseldorf, Germany

[21] Appl. No.: 750,762

[22] PCT Filed: Jun. 6, 1995

[86] PCT No.: PCT/EP95/02146

§ 371 Date: Dec. 13, 1996

§ 102(e) Date: Dec. 13, 1996

[87] PCT Pub. No.: WO95/34528

PCT Pub. Date: Dec. 21, 1995

[30] Foreign Application Priority Data

Jun. 13, 1994 [DE] Germany ............... G 44 20 516.3

[51] Int. Cl.⁶ ............... C07C 51/00; A01N 25/00
[52] U.S. Cl. ............... 554/166; 554/163; 514/772; 514/844
[58] Field of Search ............... 554/166, 163; 514/772, 844

[56] References Cited

U.S. PATENT DOCUMENTS

| | | | |
|---|---|---|---|
| 3,547,828 | 12/1970 | Mansfield | 252/351 |
| 3,707,535 | 12/1972 | Lew | 260/210 |
| 3,772,269 | 11/1973 | Lew | 260/210 |
| 3,839,318 | 10/1974 | Mansfield | 260/210 |
| 4,349,669 | 9/1982 | Klahr et al. | 536/127 |
| 4,988,456 | 1/1991 | Takahashi et al. | 252/314 |
| 5,391,321 | 2/1995 | Grüning et al. | 252/309 |

FOREIGN PATENT DOCUMENTS

| | | |
|---|---|---|
| 077 167 | 4/1983 | European Pat. Off. . |
| 440 203 | 8/1991 | European Pat. Off. . |
| 559 013 | 9/1993 | European Pat. Off. . |
| 1 165 574 | 3/1964 | Germany . |
| 1 943 689 | 3/1970 | Germany . |
| 2 036 472 | 2/1971 | Germany . |
| 20 24 051 | 12/1971 | Germany . |
| 30 01 064 | 7/1981 | Germany . |
| 40 29 323 | 3/1992 | Germany . |
| 41 17 033 | 11/1992 | Germany . |
| 04 178 316 | 6/1992 | Japan . |
| 1 524 782 | 9/1978 | United Kingdom . |
| WO 85/04346 | 10/1985 | WIPO . |

*Primary Examiner*—Paul J. Killos
*Attorney, Agent, or Firm*—Ernest J. Szoke; Wayne C. Jaeschke; Real J. Grandmaison

[57] ABSTRACT

A process for making a polyglycerol polyhydroxystearate comprising esterifying a polyhydroxystearic acid having a degree of self-condensation of from 2 to 20 with a polyglycerol component, the polyglycerol component consisting of: (a) from 5 to 30% by weight of a glycerol; (b) from 15 to 40% by weight of a diglycerol; (c) from 10 to 30% by weight of a triglycerol; (d) from 5 to 20% by weight of a tetraglycerol; (e) from 2 to 10% by weight of a pentaglycerol; and (f) remainder, up to 100%, of an oligoglycerol.

16 Claims, No Drawings

POLYOLPOLYHYDROXYSTEARATES

BACKGROUND OF THE INVENTION

1. Field of the Invention

This invention relates to new polyolpolyhydroxystearates obtainable by esterification of polyhydroxystearic acid with polyols, preferably technical polyglycerol of defined composition, to a process for their production, to formulations containing these substances and to the use of the new polyolpolyhydroxystearates as w/o emulsifiers.

2. Discussion of Related Art

Polyglycerol polyricinoleates have long been known as w/o emulsifiers and may be used for the formulation of low-viscosity w/o emulsions [cf. EP-A1 0559013 (Th. Goldschmidt), EP-A1 0440203 (Lotte Co.) and WO 85/04346 (Meiji Milk Prods.)]. However, it has been found that commercial polyglycerol polyricinoleates do not form emulsions with all the oils typically used in the cosmetics field, but only with those oils which fall within a certain polarity range. In addition, these emulsions are limited in their storage life. A major disadvantage is above all the fact that the commercial products are incapable of sufficiently stabilizing emulsions containing highly polar oils, for example vegetable oils. However, this is commercially desirable in view of the particular ecotoxicological compatibility of such emulsions.

Now, the problem addressed by the present invention was to provide new w/o emulsifiers which would form storable emulsions with a broad range of oils.

DESCRIPTION OF THE INVENTION

The present invention relates to polyolpolyhydroxystearates which are obtained by esterifying polyhydroxystearic acid with a degree of self-condensation of 2 to 20 and preferably 2 to 10 with polyols in known manner.

It has surprisingly been found that condensation products of polyols, preferably technical polyglycerol, with polyhydroxystearic acid have distinctly better emulsifying properties than comparable known products based on polyricinoleic acid. In particular, it is even possible to introduce highly polar vegetable oils into stable emulsions. The present invention also includes the observation that even the addition of small quantities of the polyolpolyhy-droxystearates according to the invention to polyolpolyricinoleates produces a lasting improvement in their emulsifying properties. It has also surprisingly been found that the condensation products based on 12-hydroxystearic acid are liquid although the acid used has a melting point of 75° C. Thus, the emulsions may readily be produced not only by the conventional "hot/hot" method, but also by the energy-saving "cold/cold" method.

In one preferred embodiment, the invention relates to polyglycerol polyhydroxystearates which are obtained by esterifying polyhydroxystearic acid having a degree of self-condensation of 2 to 20 and preferably 2 to 10 with a polyglycerol mixture of the following composition (GC method):

Glycerol: 5 to 35 (15 to 30)% by weight
Diglycerols: 15 to 40 (20 to 32)% by weight
Triglycerols: 10 to 35 (15 to 25)% by weight
Tetraglycerols: 5 to 20 ( 8 to 15)% by weight
Pentaglycerols: 2 to 10 ( 3 to 8)% by weight
Oligoglycerols: to 100% by weight
in known manner (the preferred ranges are shown in brackets).

The present invention also relates to a process for the production of polyolpolyhydroxystearates in which polyhydroxystearic acid with a degree of self-condensation of 2 to 20 and preferably 2 to 10 is esterified with polyols in known manner.

Polyols

Polyols in the context of the invention are substances which contain at least 2, preferably 3 to 12 and more preferably 3 to 8 hydroxyl groups and 2 to 12 carbon atoms. Typical examples are:

glycerol,
alkylene glycols, for example ethylene glycol, diethylene glycol, propylene glycol;
polyglycerol;
methylol compounds, more particularly trimethylol ethane, trimethylol propane, trimethylol butane, pentaerythritol and dipentaerythritol;
alkyl glucosides containing 1 to 22, preferably 1 to 8 and more preferably 1 to 4 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
aminosugars, for example glucamine.

Polyglycerol

Among the new emulsifiers, particular significance is attributed to reaction products based on polyglycerol by virtue of their excellent performance properties. It has proved to be of particular advantage to use selected polyglycerols which have the following homolog distribution (the preferred ranges are shown in brackets);

Glycerol: 5 to 35 (15 to 30)% by weight
Diglycerols: 15 to 40 (20 to 32)% by weight
Triglycerols: 10 to 35 (15 to 25)% by weight
Tetraglycerols: 5 to 20 ( 8 to 15)% by weight
Pentaglycerols: 2 to 10( 3 to 8)% by weight
Oligoglycerols: to 100% by weight Production of the Polvolpolyhydroxystearates The polyolpolyhydroxystearates may be produced in known manner. In the case of polyglycerol polyhydroxystearates, the polyglycerol is preferably prepared first followed by the polyhydroxystearic acid and, finally, the two are esterified.

The production of a polyglycerol with the composition shown above may be carried out by the self-condensation of glycerol in the presence of suitable catalysts, for example potassium carbonate, silicates according-to DE-A1 4029323 (Henkel) or borates according to DE-A1 4117033 (Henkel), at temperatures in the range from 200° to 260° C.

The polyhydroxystearic acid is prepared, for example, by alkali-catalyzed polycondensation of hydroxystearic acid, preferably 12-hydroxystearic acid obtained by hydrogenation of ricinoleic acid or technical castor oil fatty acid. Linear esterification products containing 2 to 10 and, more particularly, 2 to 8 fatty acid units are preferably formed. The following distribution (GPC method) is typically achieved:

Monomers: 1 to 10% by weight
Dimers: 5 to 15% by weight
Trimers: 5 to 15% by weight
Tetramers: 5 to 15% by weight
Pentamers: 5 to 15% by weight
Hexamers: 5 to 15% by weight
Heptamers: 5 to 15% by weight
Octamers: 1 to 10% by weight
Oligomers: to 100% by weight In one preferred embodiment of the invention, mixtures of hydroxystearic acid and ricinoleic acid or technical castor oil fatty acid, of which about 90% by weight consists of ricinoleic acid, in a ratio by weight of 99:1 to 1:99 and preferably 75:25 to 10:90 are used. Similarly, the acids may be individually condensed and the condensates subsequently mixed.

In the subsequent condensation of the polyol component, for example the polyglycerol, with the polyhydroxystearic acid or the mixtures with polyricinoleic acid, a complex mixture of homologous polyesters is formed. The percentage contents of mono-, di-, tri- and oligoesters in the polyolpoly-hydroxystearates and, preferably, polyglycerol polyhydroxystearates according to the invention are determined by the ratios in which the starting compounds are used. In one preferred embodiment of the process according to the invention, a polyolpolyhydroxystearate with particularly advantageous performance properties is obtained by subjecting around 1000 kg of 12-hydroxystearic acid to self-condensation until a product with an acid value of 50 to 55 is obtained and then esterifying this product with around 150 kg of polyglycerol with the composition shown above until the acid value has fallen to below 2.

Condensation products based on polyglycerol and polyhydroxystearic acid or polyhydroxystearic acid/polyricinoleic acid may be characterized by their iodine value. Typical examples are polyesters having an iodine value of<10 (basis: 100% 12-hydroxystearic acid) or 65 to 80 (basis: 90% 12-hydroxystearic acid, 10% ricinoleic acid).

Cosmetic and pharmaceutical formulations

The present invention also relates to cosmetic and/or pharmaceutical formulations containing the new polyolpolyhydroxystearates and, in particular, the polyglycerol polyhydroxystearates.

Another preferred embodiment of the invention relates to cosmetic and/or pharmaceutical formulations containing polyolpolyhydroxystearates, more particularly polyglycerol polyhydroxystearates, and polyolpolyricinoleates, more particularly polyglycerol polyricinoleates, in a ratio by weight of 99:1 to 1:99 and preferably in a ratio by weight of 75:25 to 10:90.

Suitable auxiliaries and additives are oils, co-emulsifiers, fats and waxes, stabilizers, thickeners, biogenic agents, film formers, fragrances, dyes, pearlescers, preservatives, UV filters, pigments, electrolytes (for example magnesium sulfate) and pH regulators.

Oils

Suitable oils are, for example, aliphatic and/or naphthenic hydrocarbons, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{6-18}$ fatty alcohols, esters of linear $C_{6-18}$ fatty acids with branched alcohols, more particularly 2-ethyl hexanol, esters of linear and/or branched fatty acids with polyhydric alcohols and/or Guerbet alcohols, triglycerides based on $C_{6-10}$ fatty acids, vegetable oils, branched primary alcohols, substituted cyclohexanes, Guerbet carbonates and/or dialkyl ethers. A factor of particular significance in this regard is that the polyglycerol polyricinoleates according to the invention are suitable for the formation of emulsions using both polar oils and also oils of medium polarity and non-polar oils with dipole moments in the range from less than 1 to more than 2.5 Debye.

Co-emulsifiers

Nonionic, ampholytic and/or zwitterionic interfacially active compounds distinguished by a lipophilic, preferably linear, alkyl or alkenyl group and at least one hydrophilic group may be used as co-emulsifiers. This hydrophilic group may be both an anionic group and a nonionic group.

Nonionic emulsifiers contain, for example, a polyol group, a polyalkylene glycol ether group or a combination of polyol and polyglycol ether groups as their hydrophilic group. Preferred formulations are those which contain as o/w emulsifiers nonionic surfactants from the group of adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group, $C_{12-18}$ fatty acid monoesters and diesters of adducts of 1 to 30 moles of ethylene oxide with glycerol, Glycerol monoesters and diesters and sorbitan monoesters and diesters of saturated and unsaturated $C_{8-18}$ fatty acids and ethylene oxide adducts thereof, $C_{8-18}$ alkyl monoglycosides and oligoglycosides and ethoxylated analogs thereof and adducts of 15 to 60 moles of ethylene oxide with castor oil and/or hydrogenated castor oil.

Mixtures of compounds from several of these classes are also suitable.

The adducts of ethylene oxide and/or propylene oxide with fatty alcohols, fatty acids, alkylphenols, glycerol monoesters and diesters and sorbitan monoesters and diesters of fatty acids or with castor oil are known commercially available products. They are mixtures of homologs of which the average degree of alkoxylation corresponds to the ratios between the quantities of ethylene oxide and/or propylene oxide and substrate with which the addition reaction is carried out.

$C_{12-18}$ fatty acid monoesters and diesters of adducts of ethylene oxide with glycerol are known from DE-PS 2024051 as refatting agents for cosmetic formulations. $C_{8-18}$ alkyl monoglycosides and oligoglycosides, their production and their use as surface-active agents are known, for example, from U.S. Pat. No. 3,839,318, U.S. Pat. No. 3,707,535, U.S. Pat. No. 3,547,828, DE-OS 1943689, DE-OS 2036472 and DE-A1 3001064 and from EP-A 0077167. They are produced in particular by reaction of glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Zwitterionic surfactants may also be used as emulsifiers. Zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acyl aminopropyl-N,N-dimethyl ammonium glycinates, for example cocoacyl aminopropyl dimethyl ammonium glycinate, and 2-alkyl-3-carboxymethyl-3-hydroxyethyl imidazolines containing 8 to 18 carbon atoms in the alkyl or acyl group and cocoacyl aminoethyl hydroxyethyl carboxymethyl glycinate. The fatty acid amide derivative known under the CTFA name of Cocamidopropyl Betaine is particularly preferred.

Ampholytic surfactants are also suitable emulsifiers. Ampholytic surfactants are surface-active compounds which, in addition to a $C_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and $C_{12-18}$ acyl sarcosine.

Suitable w/o emulsifiers are:

adducts of 2 to 15 moles of ethylene oxide and castor oil and/or hydrogenated castor oil;

partial esters based on linear, branched, unsaturated or saturated $C_{12-22}$ fatty acids, ricinoleic acid and 12-hydroxystearic acid and glycerol, polyglycerol, pentaerythritol, dipentaerythritol, sugar alcohols, (for example sorbitol) and polyglucosides (for example cellulose);

trialkyl phosphates;

wool wax alcohols;

polysiloxane/polyalkyl polyether copolymers and corresponding derivatives;

mixed esters of pentaerythritol, fatty acids, citric acid and fatty alcohol according to DE-PS 1165574 and polyalkylene glycols.

Other additives

Typical examples of fats are glycerides while suitable waxes are inter alia beeswax, paraffin wax or microwaxes, optionally in combination with hydrophilic waxes, for example fatty alcohols, monoglycerides and fatty acids.

Suitable stabilizers are metal salts of fatty acids, for example magnesium, aluminium and/or zinc stearate.

Suitable thickeners are, for example, crosslinked polyacrylic acids and derivatives thereof, polysaccharides, more particularly xanthan gum, guar guar, agar agar, alginates and tyloses, carboxymethyl cellulose and hydroxyethyl cellulose, polyacrylates, polyvinyl alcohol and polyvinyl pyrrolidone.

Biogenic acids in the context of the invention are, for example, plant extracts, protein hydrolyzates and vitamin complexes. Typical film formers are, for example, hydrocolloids, such as chitosan, microcrystalline chitosan or quaternized chitosan, polyvinyl pyrrolidone, vinyl pyrrolidone/vinyl acetate copolymers, polymers of the acrylic acid series, quaternary cellulose derivatives and similar compounds.

Suitable preservatives are, for example, formaldehyde solution, p-hydroxybenzoate or sorbic acid.

Suitable pearlescers are, for example, glycol distearic acid esters, such as ethylene glycol distearate, and fatty acids and fatty acid monoglycol esters.

Suitable dyes are any of the substances suitable and permitted for cosmetic purposes as listed, for example, in the publication entitled "Kosmetische Färbemittel" of the Farbstoffkommission der Deutschen Forschungsgemeinschaft, published by Verlag Chemie, Weinheim, 1984. These dyes are normally used in concentrations of 0.001 to 0.1% by weight, based on the mixture as a whole.

The percentage content of auxiliaries and additives may be from 0.01 to 80% by weight and is preferably from 0.05 to 40% by weight while the non-aqueous component ("active substance") makes up from 20 to 80% by weight and preferably from 30 to 70% by weight of the particular formulation. The formulations may be prepared by known methods, i.e. for example by hot, cold, hot-hot/cold or PIT emulsification. These are purely mechanical processes which do not involve a chemical reaction.

Commercial Applications

The polyolpolyhydroxystearates according to the invention are distinguished by improved emulsifying power. The resulting emulsions have higher stability in storage and, in particular, higher heat resistance than known products.

Accordingly, the present invention also relates to the use of the polyolpolyhydroxystearates according to the invention in general and the polyglycerol polyhydroxystearates in particular, optionally in admixture with polyglycerol polyricinoleates, as w/o emulsifiers for cosmetic and/or pharmaceutical formulations such as, for example, skin cremes, body lotions, sunscreens and the like, in which they may be present in concentrations of 1 to 20% by weight and preferably 2 to 10% by weight, based on the particular product.

EXAMPLES

I. Polyolpolyhydroxystearates used

A) Polyglycerol polyricinoleate, I.V.=85 (comparison)

B) Polyglycerol polyester based on a starting fatty acid mixture of 9 parts by weight of ricinoleic acid and 1 part of 12-hydroxystearic acid; I.V.=75

C) Polyglycerol polyester consisting of 9 parts by weight of polyglycerol polyricinoleate and 1 part by weight of polyglycerol polyhydroxy-stearate; I.V.=75

D) Polyglycerol polyhydroxystearate; I.V.<10

The composition of the polyglycerol components was 20% by weight glycerol, 30% by weight diglycerols, 20% by weight triglycerols, 15% by weight tetraglycerols, 5% by weight pentaglycerols and 10% by weight oligoglycerols.

The composition of the polyhydroxyfatty acid was 5% by weight monomers, 10% by weight dimers up to heptamers, 6% by weight octamers and ad 100% by weight oligomers.

Products B, C and D correspond to the invention while product A is intended for comparison.

II. Performance tests

The properties of emulsifiers B, C and D according to the invention and comparison emulsifier A were tested in various w/o emulsions according to Table 1. Formulations F1 to F3 correspond to the invention while formulation F4 is intended for comparison. The viscosity of the products was determined after storage (1 day, 1 week and 4 weeks) at 23° C. using a Brookfield RVF viscosimeter, spindle 5, 10 r.p.m. The results are set out in Table 2.

TABLE 1

Formulations Used

|  | F1 % | F2 % | F3 % | F4 % |
|---|---|---|---|---|
| Emulsifier A | — | — | — | 7.0 |
| Emulsifier B | 7.0 | — | — | — |
| Emulsifier C | — | 7.0 | — | — |
| Emulsifier D | — | — | 7.0 | — |
| Almond oil | 20.0 | 20.0 | 20.0 | 20.0 |
| Glycerol, 86% by weight | 5.0 | 5.0 | 5.0 | 5.0 |
| MgSO$_4$.7H$_2$O | 0.5 | 0.5 | 0.5 | 0.5 |
| Formaldehyde | 0.1 | 0.1 | 0.1 | 0.1 |
| Water | To 100% | | | |

TABLE 2

Results of Performance Tests

| | Viscosity [mPa.s] | | | Stability | |
|---|---|---|---|---|---|
| Formulation | 1d | 1w | 4w | 1w | 4w |
| F1 | 20000 | 19600 | 20000 | Stable | Stable |
| F2 | 20800 | 20800 | 20000 | Stable | Stable |

TABLE 2-continued

Results of Performance Tests

| Formulation | Viscosity [mPa.s] | | | Stability | |
| --- | --- | --- | --- | --- | --- |
| | 1d | 1w | 4w | 1w | 4w |
| F3 | 15200 | 14000 | 14000 | Stable | Stable |
| F4 | — | — | — | Does not emulsify | |

III. Formulation Examples

| I) | Cosmetic skin lotion | |
| --- | --- | --- |
| | Product D | 3% by weight |
| | Monomuls ® 90-0 18 | 1% by weight |
| | Beeswax | 1% by weight |
| | Cetiol ® OE | 5% by weight |
| | Cetiol ® LC | 6% by weight |
| | Jojoba oil | 12% by weight |
| | Glycerol | 5% by weight |
| | MgSO$_4$.7H$_2$O | 1% by weight |
| | Formalin | 0.15% by weight |
| | Water | ad 100% by weight |
| | Viscosity | 8,000 mPa.s |
| II) | Cosmetic nourishing creme | |
| | Product D | 4% by weight |
| | Lameform ® TGI | 4% by weight |
| | Beeswax | 3% by weight |
| | Almond oil | 20% by weight |
| | Glycerol | 5% by weight |
| | MgSO$_4$.7H$_2$O | 1% by weight |
| | Formalin | 0.15% by weight |
| | Water | ad 100% by weight |
| | Viscosity | 700,000 mPa.s |

The viscosities of the two products were determined with a Brookfield RVF viscosimeter at 23° C. Spindle 5, (10 r.p.m.) was used for product I while spindle E (4 r.p.m., with Helipath) was used for product II.

The product names Monomuls® 90-0 18, Cetiol® OE, Cetiol® LC and Lameform® TGI stand respectively for oleic acid monoglyceride, di-n-octyl ether, $C_{8/10}$-fatty acid-$C_{12/18}$-cocoalkyl ester and triglycerol triisostearate, all produced by Henkel KGaA of Düsseldorf FRG.

We claim:

1. A process for making a water-in-oil emulsifier comprising esterifying a polyhydroxystearic acid component having a degree of self-condensation of from 2 to 20 with a polyglycerol component, the polyglycerol component consisting of:
    (a) from 5 to 30% by weight of a glycerol;
    (b) from 15 to 40% by weight of a diglycerol;
    (c) from 10 to 30% by weight of a triglycerol;
    (d) from 5 to 20% by weight of a tetraglycerol;
    (e) from 2 to 10% by weight of a pentaglycerol; and
    (f) remainder, up to 100%, of an oligoglycerol.

2. The process of claim 1 wherein the polyhydroxystearic acid is obtained by alkalicatalyzed polycondensation of hydroxystearic acid.

3. The process of claim 2 wherein the hydroxystearic acid is 12-hydroxystearic acid.

4. The process of claim 3 wherein the 12-hydroxystearic acid is obtained by hydrogenation of an acid component selected from the group consisting of ricinoleic acid and technical castor oil fatty acid.

5. The process of claim 1 wherein the polyhydroxystearic acid has a molecular distribution, as determined by gel permeation chromatography, of:
    (a) 1 to 10% by weight of monomers;
    (b) 5 to 15% by weight of dimers;
    (c) 5 to 15% by weight of trimers;
    (d) 5 to 15% by weight of tetramers;
    (e) 5 to 15% by weight of pentamers;
    (f) 5 to 15% by weight of hexamers;
    (g) 5 to 15% by weight of heptamers;
    (h) 1 to 10% by weight of octamers; and
    (i) remainder, up to 1.00% by weight, of oligomers.

6. The process of claim 1 wherein the polyhydroxystearic acid comprises a mixture of hydroxystearic acid and an acid component selected from the group consisting of ricinoleic acid and technical castor oil fatty acid, in a ratio by weight of from 99:1 to 1:99.

7. The product of the process of claim 1.

8. The product of the process of claim 2.

9. The product of the process of claim 3.

10. The product of the process of claim 4.

11. The product of the process of claim 5.

12. The product of the process of claim 6.

13. A cosmetic formulation comprising a water-in-oil emulsifier consisting essentially of a polyglycerol polyhydroxystearate.

14. The cosmetic formulation of claim 13 further comprising a polyglycerol polyricinoleate in combination with the polyglycerol polyhydroxystearate in a ratio by weight of from 99:1 to 1:99.

15. A pharmaceutical formulation comprising a water-in-oil emulsifier consisting essentially of a polyglycerol polyhydroxystearate.

16. The pharmaceutical formulation of claim 15 further comprising a polyglycerol polyricinoleate in combination with the polyglycerol polyhydroxystearate in a ratio by weight of from 99:1 to 1:99.

* * * * *